(12) United States Patent
Yarosh

(10) Patent No.: US 6,479,533 B1
(45) Date of Patent: Nov. 12, 2002

(54) METHODS AND COMPOSITIONS FOR THE PROTECTION OF MITOCHONDRIA

(75) Inventor: Daniel B. Yarosh, Merrick, NY (US)

(73) Assignee: Applied Genetics Incorporated Dermatics, Freeport, NY (US)

( * ) Notice: Subject to any disclaimer, the term of this patent is extended or adjusted under 35 U.S.C. 154(b) by 0 days.

(21) Appl. No.: 09/452,585

(22) Filed: Dec. 1, 1999

Related U.S. Application Data

(62) Division of application No. 09/026,875, filed on Feb. 20, 1998, now Pat. No. 6,103,746.
(60) Provisional application No. 60/038,749, filed on Feb. 20, 1997.

(51) Int. Cl.$^7$ ............................................... A61K 3/415
(52) U.S. Cl. ...................................... 514/398; 424/9.1
(58) Field of Search ........................... 514/398; 424/9.1

(56) References Cited

U.S. PATENT DOCUMENTS

| | | | |
|---|---|---|---|
| 4,898,878 A | | 2/1990 | Shapiro et al. |
| 5,190,762 A | | 3/1993 | Yarosh |
| 5,272,166 A | | 12/1993 | Breslow et al. |
| 5,438,151 A | | 8/1995 | Yadan et al. |
| 5,728,373 A | | 3/1998 | Alert et al. |
| 5,788,988 A | * | 8/1998 | Soon-Shiong et al. ...... 424/484 |
| 6,010,890 A | * | 1/2000 | Ben-Hur et al. .......... 435/173.3 |
| 6,103,746 A | | 8/2000 | Yarosh |

FOREIGN PATENT DOCUMENTS

| | | |
|---|---|---|
| JP | 61 155302 | 7/1986 |
| JP | 63 008335 | 1/1988 |
| WO | WO 94/04129 | 3/1994 |

OTHER PUBLICATIONS

Akanmu et al., "The Antioxidant Action of Ergothioneine," *Arch. Biochem. Biophys.* 288:10–16, 1991.
Brummel, M.C., "In search of a Physiological Function for L–Ergothioneine," *Medical Hypotheses*, 18:351–370, 1985.
Brummel, M.C., "In search of a Physiological Function for L–Ergothioneine–II," *Medical Hypotheses*, 30:39–48, 1989.
Dahl et al., "Some Prevalent Biomolecules as Defenses Against Singlet Oxygen Damage," *Photochemistry and Photobiology*, 47:357–362, 1988.
Gregoriadis, 1993, "Liposome Technology", CRC Press, Boca Raton, Florida.
Hartman et la, "Interception of Some Direct–Acting Mutagens by Ergothioneine," *Environmental and Molecular Mutagenesis*, 10:3–15, 1987.
Hartman et al., "Ergothioneine, Histidine, and Two Naturally Occurring Histidine Dipeptides as Radioprotectors against γ–Irradiation Inactivation of Bacteriophages T4 and P22," *Radiation Research* 114:319–330, 1988.
Hartman, P., "Ergothioneine as Antidioxidant," *Methods in Enzymology*, 186:310–318, 1990.

Jovanovic et al., "Free Radical Chemistry of Ergothioneine, a Potential Radioprotector and Antimutagen," *Anticarcinogenesis and Radiation Protection 2*, (Conference Proceedings), O.F. Nygaard and A.C. Upton editors, Plenum Press, New York, 229–235, 1991.

Kawano et al., "Studies on ergothioneine. XI. Inhibitory Effect on Lipid Peroxide Formation in Mouse Liver," *Chem. Pharm. Bull.*, 31:1682–1687 (1983).

Langer, "New Methods of Drug Delivery," *Science*, 249:1527–1533, 1990.

Lopez–Berestein, "Treatment of Systemic Fungal Infections with Liposomal–Amphotericin B," in *Liposomes in the Therapy of Infectious Disease and Cancer*, Lopez–Berestein and Fidler editors, Alan R. Liss, Inc., New York, pp. 317–327, 1989.

Melville, D., "Ergothioneine," *Vitamins and Hormones* 7:155–204, 1959.

Motohashi et al., "Effect of Ergothioneine on γ–Irradiation of Metmyoglobin," *Radioisotopes*, 22:451–452, 1973.

Nishigori et al., "Effect of MPG on Glucocorticoid–Induced Cataract Formation in Developing Chick Embryo," *Investigative Ophthalmology & Visual Science*, 25:1051–1055, 1984.

Poznansky et al., "Biological Approaches to the Controlled Delivery of Drugs: A Critical Review," *Pharmacological Reviews*, 36:277–335, 1984.

Rosenthal et al., "Role of oxygen in the phototoxicity of phthalocyanines," *Int. J. Radiat. Biol.*, 67:85–91, 1995.

Rougee et al., "Deactivation of Singlet Molecular Oxygen by Thiols and Related compounds, Possible Protectors Against Skin Photosensitivity," *Photochemistry and Photobiology*, 47:485–489, 1988.

(List continued on next page.)

*Primary Examiner*—James H. Reamer
(74) *Attorney, Agent, or Firm*—Maurice M. Klee

(57) ABSTRACT

Protection of mitochondria from oxidative damage due to natural or disease processes as well as by the effects of exogenous factors such as incident sunlight, exposure via inhalation to oxidative environmental toxins, consumption of dietary oxidants, and oxidative-stress-inducing cosmetics and pharmaceuticals, radiation therapy, among others, is provided by a composition comprising L-ergothioneine, L-ergothioneine may be prepared in a cosmetically or pharmaceutically-acceptable base to form an agent for topical application to the skin, and for oral or parenteral administration. Effective application and delivery, of L-ergothioneine is enhanced by encapsulation in a liposomes, a preferred embodiment. Diagnostic methods for determining exposure and susceptibility to radiation, radical and reactive oxygen species in mammals is also provided.

5 Claims, No Drawings

OTHER PUBLICATIONS

Rywkin et al. "Importance of Type I and Type II Mechanisms in the Photodynamic Inactivation of Viruses in Blood with Aluminum Phthalocyanine Derivatives," *Photocem Photobiol.*, 56:463–469, 1992.

Treat et al., in *Liposomes in the Therapy of Infectious Disease and Cancer*, Lopez–Berestein and Fidler (eds.) Liss: New York, pp. 353–365, 1989.

van den Broeke et al., "Thiols as potential UV radiation protectors: an in vitro study," *J. Photochem. Photobiol. B: Biol.*, 1993, 17:279–286.

van den Broeke et al., "UV–radiation protecting efficacy of thios, studied with UVA–induced binding of 8–MOP and CPZ to rat epidermal biomacromolecules in vivo," *Int. J. Radiat. Biol.*, 1993, 63:493–500.

Aruoma, et al., "Antioxidant Action of Ergothioneine: Assessment of Its Ability to Scavenge Peroxynitrate," *Biochem. Biophys. Res. Comm.*, (1997) 231:389–391.

Asmus, et al., "One–electron oxidation of ergothioneine and analogues investigated by pulse radiolysis: redox reaction involving ergothioneine and vitamin C," *Biochem. J.* (1996) 315:625–629.

* cited by examiner

METHODS AND COMPOSITIONS FOR THE PROTECTION OF MITOCHONDRIA

CROSS REFERENCE TO RELATED APPLICATIONS

This is a divisional application of U.S. Application Ser. No. 09/026,875, filed on Feb. 20, 1998, now U.S. Pat. No. 6,103,746, which claims the benefit under 35 USC §119(e) of U.S. Provisional Application No. 60/038,749 filed Feb. 20, 1997, the contents of both of which in their entireties are hereby incorporated by reference.

BACKGROUND OF THE INVENTION

Mitochondria are subcellular organelles present: in all oxygen-utilizing eukaryotic organisms in which energy in the form of adenosine triphosphate (ATP) is generated, and oxygen is reduced to water. Ninety percent of the oxygen taken in is consumed in mitochondria. A substantial byproduct of this ATP generation is the formation of potentially toxic oxygen radicals. For example, it is estimated that 1–2% of all reduced oxygen yields superoxide ($O_2$—) and hydrogen peroxide ($H_2O_2$). Other reactive oxygen species (ROS) that form are singlet oxygen ($^1O_2$) and hydroxyl radical (OH•). Under stress conditions in the cell this can rise to 10% of all consumed oxygen. Mitochondrial membranes are sensitive to lipid peroxidation and depolarization resulting from these ROS. Mitochondrial damage is also a result of exposure to sunlight, which forms ROS as indicated above. Because damage to mitochondria is believed to be the cause or an important factor in some diseases, such as cancer, diabetes, cataract, neurodegenerative disease, porphyrias, cardiovascular disease, and also a contributor to the complications of aging, a method of protecting mitochondria from such damage, repairing such damage, is desired. Furthermore, exposure to adverse environmental factors, including industrial air pollutants and petroleum and tobacco combustion products, may contribute to oxidative damage to pulmonary and other tissues of the body. In addition, various therapeutic regimens such as chemotherapeutic drugs and radiation therapy for the treatment of dysproliferative diseases induce significant oxidant stress-related side effects, such as cardiotoxicity. The present invention relates to applied agents which protect the mitochondria from such damage.

Eukaryotic (e.g. plant and animal) cells differ from prokaryotic cells (e.g. bacteria, viruses and the like) in that they contain mitochondria. To the extent that damage to mitochondria is debilitating to eukaryotic cells, they are hypersensitive to this damage relative to prokaryotic cells. Treatments designed to inactivate such bacteria and viruses by ROS, such as photodynamic therapy (PDT, treatment of cells with pro-dyes or dyes followed by exposure to light) have the unwanted side effects of damaging the mitochondria of the host non-diseased cells. The present invention relates to reducing the toxicity of ROS to mitochondria, and thus improving the therapeutic index of therapies utilizing ROS to inactivate prokaryotic organisms.

In some cases one portion of tissue is the target for inactivation by ROS while the surrounding tissue should be spared. For example, the hair and hair follicle are targets for PDT and so-called photothermolysis therapy while the surrounding skin should be preserved. The present invention relates to protection of the mitochondria in the surrounding tissue and thus enhancing the relative efficacy of the cosmetic or therapeutic treatment in inactivating target tissue.

L-ergothioneine is a sulphur-containing amino acid that is found in many mammalian tissues but is not endogenously synthesized and must be consumed in the diet. By L-ergothioneine I include ergothioneine and all its derivatives and congeners that in aqueous solution are 2-thio-imidazoles and are predominantly in the thione rather than the thiol form. L-ergothioneine exists in some tissues in millimolar quantities, its exact role is uncertain (see: Melville, 1959, Vitamins and Hormones 7:155–204). It is generally regarded as an antioxidant, although results are conflicting. Some regard it as a scavenger of hydrogen peroxide (see: Hartman, 1990, Methods in Enzymology 186:310–318) while others contend that it does not readily react with hydrogen peroxide but does scavenge hydroxyl radical (see: Akamnu et al. 1991, Arch. Biochem. Biophys. 298:10–16, 1991). Although previous in vitro studies have demonstrated its ability to protect DNA and proteins against phototoxic drug binding induced by UV radiation. (e.g., van den Brooke et al., 1993, J. Photochem. Photobiol. B 17:279–286), and to protect bacteriophage against gamma-irradiation (Hartman et al., 1988, Radiation Research 114:319–330), in vivo results have not been as promising. Although L-ergothioneine has been claimed as useful in topical formulations for scavenging radicals and UV light protectants for hair a skin damage (e.g., WO 9404129), Van den Broeke et al. (1993, mnt. J. Radiat. Biol. 63:493–500) did not find topically applied L-ergothioneine effective in an animal model of UV-induced phototoxic drug binding to epidermal biomolecules. Other proposed in vivo uses have included lowering of circulating lipoprotein (a) levels (U. S. Pat. No. 5,272,166), and inhibiting skin pigmentation, for example, to remove dark spots and freckles (JP 63008335 and JP 61155302).

As described above, numerous disease processes are attributed to the body's adverse reaction to the presence of elevated levels of reactive oxygen species (ROS) described above. In the eye, cataract, macular degeneration and degenerative retinal damage are attributed to ROS. Other organs and their ROS-related diseases include: lung cancer induced by tobacco combustion products and asbestos; accelerated aging and its manifestations, including skin damage; atherosclerosis; diseases of the nervous system such as Parkinson's disease, Alzheimer's disease, muscular dystrophy, multiple sclerosis; other lung diseases including emphysema and bronchopulmonary dysphasia; iron overload diseases such as hemochromatosis and thalassemia; pancreatitis; diabetes; renal diseases including autoimmune nephrotic syndrome and heavy metal-induced nephrotoxicity; and radiation injuries. Certain anti-neoplastic drugs such as adriamycin and bleomycin induce severe oxidative damage, especially to the heart, limiting the patient's exposure to the drugs. Redox-active metals such as iron induce oxidative damage to tissues; industrial chemicals and ethanol, by exposure and consumption, induce an array of oxidative damage-related injuries, such as cardiomyopathy and liver damage. Airborne industrial and petrochemical-based pollutants, such as ozone, nitric oxide, and halogenated hydrocarbons, induce oxidative damage to the lungs, gastrointestinal tract, and other organs. Protecting mitochondria from these many etiologic agents is desirable.

Photodynamic therapy (PDT) is the use of light, especially laser light, to activate a chromophore to produce ROS, which can be either endogenous (melanin, hemoglobin) or exogenous (applied dye or pro-dye metabolized or converted to a dye) for the purpose of destroying a target with ROS. PDT is used to kill diseased cells such as tumor cells, but it is also used to destroy non-eukaryotic cellular targets such as viruses and hair. An unwanted side-effect of PDT to destroy non-eukaryotic cellular targets is the destruction of living eukaryotic cells by destruction of their mitochondria, such as red blood cells or epidermal cells. This unwanted cell killing is the limiting factor in the usefulness of these PDT therapies in applications such as blood sterilization and laser hair removal. In general Type I oxidation reactions lead to lipid peroxidation that damage mitochondria while singlet oxygen (Type II reactions) destroy non-cellular targets (see I. Rosenthal and E. Ben-Hur, Int. J. Radiat. Biol., 1995, 67:85, and S. Rywkin, L. Lenny, J. Goldstein, N. Geacintov, H. Margolis-Nunno and B. Horowitz, Photochem. Photobiol. 1992, 56:463). The invention conceives of the use of L-ergothioneine to selectively quench Type I oxidation reactions while not interfering with singlet oxygen (Type II reactions).

Inactivation of viruses, such as HIV, by PDT involves the generation of singlet oxygen that is toxic to the virus. However, if the viral inactivation occurs in the presence of living cells, such as blood cells, the cellular components (red and white blood cells) can be damaged by Type I reactions. Another example is light activated hair removal, the so-called selective photothermolysis. In this process light is selected that matches the melanin-absorbing wavelengths of the hair or to a photosensitizer that can be selectively accumulated on the hair or in the hair follicle. An unwanted side effect is damage to cells that also contain the chromophore, such as melanin-bearing or covered cells in the epidermis or epidermal cells that have inadvertently absorbed the applied photosensitizer. These cells are damaged by Type I photoreactions.

These problems can be overcome by using L-ergothioneine to selectively quench Type I reactions that destroy mitochondria but not Type II reactions. It has been reported in the literature that L-ergothioneine quenches singlet-oxygen, teaching away from the present invention, or prevents generation of singlet oxygen, while others contradict these results. The literature teaches away from using L-ergothioneine during viral inactivation by radiation since it is reported to protect bacteriophage T4 and P22 from inactivation by γ-radiation.

SUMMARY OF THE INVENTION

It is an objective of the present invention to provide a means for protecting mitochondria from damage by providing methods and compositions by which mammalian mitochondrial membranes are protected.

It is another objective of the invention to provide methods and compositions by which mammalian mitochondria can be protected from oxidative damage.

It is a further objective of the invention to provide methods and compositions which protect mammalian mitochondria from being damaged by the effects of incident sunlight as well as other damaging radiation, and agents that sensitize cells to radiation through PDT or so-called photothermolysis.

It is yet a further objective of the invention to provide methods and compositions which protect mammalian mitochondria from being damaged by the effects of airborne oxidative toxins, such as are present in industrial pollutants and in petrochemical and tobacco combustion products.

It is as yet another objective of the invention to provide methods and compositions which protects mammalian mitochondria from being damaged by the effects of elevated levels of oxidative compounds and ROS which occur in various disease processes, as well as that induced by various therapeutic agents and regimens.

It is another object of the present invention to provide diagnostic tests for determining in a mammal the extent and susceptibility to mitochondrial damage from radiation, radicals, and ROS.

Mitochondria are damaged by oxidative damage due to natural and disease processes as well as by the effects of exogenous factors such as incident sunlight, exposure via inhalation to oxidative environmental toxins, consumption of dietary oxidants and oxidative stress-inducing pharmaceuticals, cosmetics, PDT and so-called photothermnolytic therapies, among others. In the present invention, pretreatment or treatment of cells with L-ergothioneine protects mitochondria from such damage and reduces the damage caused to mitochondria by sunlight and that caused by the presence of oxygen radicals. In one non-limiting example, L-ergothioneine is combined in an aesthetically or pharmaceutically acceptable base to form an agent for topical application to the skin. The invention includes methods for treatment using L-ergothioneine administered orally or parenterally. Effective application and delivery of L-ergothioneine is enhanced by encapsulation in a liposome, a preferred embodiment. In one example, a liposome composed of phosphatidyl choline, phosphatidyl ethanolamine, oleic acid and cholesteryl hemisuccinate is used. The liposome-encapsulated L-ergothioneine is also combined with an aesthetically or pharmaceutically-acceptable base for topical application.

DETAILED DESCRIPTION OF THE INVENTION

Inhibition of oxidative damage to mitochondria in various tissues of the mammalian body is of therapeutic benefit for the prophylaxis and treatment of many pathological conditions ranging from those responsible for significant morbidity and mortality, such atherosclerosis and cancer, to those of a less pathological but significant adverse psychological component, such as unsightly changes to the skin as a result of long-term photoaging. In diverse diseases such as cancer, diabetes, atherosclerosis, cataract, and certain neurological diseases, among others, ROS are implicated in the pathophysiology of the disease. Cancer chemotherapeutic agents such as adriamycin and bleomycin induce oxidant damage, as does anti-cancer radiation (e.g., X-ray) therapy. Therapies that use light combined with endogenous and exogenous chromophores and photosensitizers that generate ROS are also used to produce cosmetic and therapeutic results by damaging mitochondria. As critical subcellular organelles involved in aerobic energy metabolism and the oxidative reactions therein, mitochondria are sensitive to endogenous and exogenous influences and may be easily damaged or destroyed. Dysfunctional energy metabolism and, more severely, damaged mitochondria, may lead to cell senescence, apoptosis and death, and downstream tissue and organ dysfunction and damage. In the skin, increased oxidative damage as a consequence of UV light exposure can damage the cellular structure of the skin leading to premature, psychologically-debilitating changes related to aging, such as thinning of the skin, wrinkling, and abnormal pigmentation. Exposure of environmental oxidants to the lungs can induce mitochondrial and attendant cellular damage leading to chronic airway obstructive disorders.

In accordance with the present invention, protection is afforded to mitochondria by the application or administration of a composition comprising L-ergothioneine. Administration to the target cells, tissue, or organ may be parenterally; transmucosally, e.g., orally, nasally, rectally; or transdermally or intradermally. Parenteral administration is via intravenous injection, and also including, but is not limited to, intraarterial, intramuscular, intradermal, subcutaneous, intraperitoneal, intraventricular, intrathecal and intracranial administration. It may be prepared in a tablet or capsule formulation for oral administration. For topical delivery, a solution of L-ergothioneine in water, buffered aqueous solution or other cosmetically or pharmaceutically acceptable carrier, or in a hydrogel lotion or cream, comprising an emulsion of au aqueous and hydrophobic phase. at a concentration of between 10 $\mu$M and 5 mM, is used. In light of the current manufacturing costs and constraints of L-ergothioneine, a preferred concentration is about 20 $\mu$M. To this may be added ascorbic acid or its salts, or other ingredients, or a combination of these, to make a cosmetically-acceptable formulation. Metals should be kept to a minimum. It may be preferably formulated by encapsulation into a liposome for oral, parenteral, or, preferably, topical administration. As will be seen below, a composition of L-ergothioneine within a liposome improves the efficacy of protection of mitochondria from oxidative damage resulting from radiation damage.

It was found unexpectedly that the use of a liposome formulation for L-ergothioneine enhances the effectiveness of the compound for the protection of mitochondria. While liposome delivery has been utilized as a pharmaceutical delivery system for many other compounds for a variety of applications [see Langer, Science, 1990, 249:1527–1533; Treat et al., in *Liposomes in the Therapy of Infectious Disease and Cancer*, Lopez-Berestein and Fidler (eds.), Liss: New York, pp- 353–365 (1989); Lopez-Berenstein, ibid., pp. 317–327; see generally ibid.], subcellular delivery of L-ergothioneine in an efficacious form was discovered by the inventor herein and is a preferred embodiment of the compositions and methods of the present invention. The function of the liposome is to increase the delivery of the L-ergothioneine to the mitochondria, and distinctly or additionally, to protect the L-ergothioneine until it reaches the target cell or tissue. A non-limiting example of a liposome formulation is that formed from phosphatidyl choline, phosphatidyl ethanolamine, oleic acid and cholesteryl hemisuccinate in a ratio of 2:2:1:5, encapsulating 10 mM L-ergothioneine. A final concentration of 1 $\mu$M to 10 $\mu$M L-ergothioneine is used, preferably about 12 $\mu$M. This final concentration can be achieved by dilution of the purified liposomes in a cosmetically or pharmaceutically-acceptable base. Many other suitable liposome formulations are known to the skilled artisan, and may be employed for the purposes of the present invention. For example, see: U.S. Pat. No. 5, 190,762; "Method of Administering Proteins to Living Skin Cells" to Yarosh which is incorporated herein by reference. A general discussion of liposomes and liposome technology can be found in a three volume work entitled "Liposome Technology" edited by G. Gregoriadis, 1993, published by CRC Press, Boca Raton, Fla. The pertinent portions of this reference are incorporated herein by reference.

Transdermal delivery of L-ergothioneine, either as a liposome formulation or free L-ergothioneine, is also contemplated. Various and numerous methods are known in the art for transdermal administration of a drug, e.g., via a transdermal patch. It can be readily appreciated that a Transdermal route of administration may be enhanced by use of a dermal penetration enhancer.

In yet another aspect of the present invention, provided is cosmetic and pharmaceutical compositions of L-ergothioneine. Such compositions may be for administration for injection, or for oral, pulmonary, nasal, topical, intradermal or transdermal or other forms of administration. In general, comprehended by the invention are cosmetic and pharmaceutical compositions comprising effective amounts of L-ergothioneine together with cosmetic or pharmaceutically acceptable diluents, preservatives, solubilizers,. emulsifiers, adjuvants and/or carriers. Such compositions include diluents of various buffer content (e.g., Tris-HCl, acetate, phosphate), pH and ionic strength; additives such as detergents and solubilizing agents (e.g. Tween 80, Polysorbate 80), moisturizing agents (e.g. ceramides, alpha-hydroxy acids) anti-oxidants (e.g., ascorbic acid, sodium metabisulfite), preservatives (e.g., phenoxyethanol, phenonip, thimerosal, benzyl alcohol) and bulking substances (e.g., lactose. manitol); incorporation of the material into particulate preparations of polymeric compounds such as polylactic acid, polyglycolic acid, etc. or into liposomes (infra). Hylauronic acid may also be used. Such compositions may influence the physical state, stability, rate of in vivo release, and rate of in vivo clearance of L-ergothioneine. The compositions may be prepared in liquid or lotion form, or may be in dried powder, such as lyophilized form, or may be prepared as an aerosol.

Controlled release oral formulation may be desirable. The drug may be incorporated into an inert matrix which permits release by either diffusion or leaching mechanisms, e.g., gums. Slowly regenerating matrices may also be incorporated into the formulation. Some enteric coatings also have a delayed release effect. Another form of a controlled release of this composition is by a method based on the Ores therapeutic system (Alza Corp), i.e. the drug is enclosed in a semipermeable membrane which allows water to enter and push drug out through a single small opening due to osmotic effects.

Also contemplated herein is pulmonary delivery of the pharmaceutical compositions of the present invention, for the treatment or promotion of mitochondria from oxidative damage. Pulmonary delivery may be used to treat the lung tissue itself, or serve as a delivery route to the blood stream and thus other locations within the body. A pharmaceutical composition of the present invention is delivered to the lungs of an animal while inhaling and traverses across the lung epithelial lining to the blood stream. Contemplated for use in the practice of this invention are a wide range of mechanical devices designed for pulmonary delivery of therapeutic products, including but not limited to nebulizers, measured dose inhalers, and powder inhalers, all of which are familiar to those skilled in the art. With regard to construction of the delivery device, any form of aerosolization known in the art, including but not limited to spray bottles, nebulization, aromization or pump aerosolization of a liquid formulation, and aerosolization of a dry powder formulation, can be used in the practice of the invention.

Ophthalmic delivery of the compositions of the present invention is also contemplated for the protection and treatment of mitochondria, for example, in the lens of the eye, in which oxidative damage is believed to account for a high incidence of cataracts. Other ophthalmic uses include treatment or prophylaxis of macular degeneration and degenerative retinal damage.

Nasal delivery of a pharmaceutical composition of the present invention is also contemplated. Nasal delivery allows the passage of a pharmaceutical composition of the present invention to the blood stream directly after, administering the therapeutic product to the nose, without the necessity for deposition of the product in the lung. Formulations for nasal delivery include those with dextran or cyclodextran. For nasal administration, a useful device is a small, hard bottle to which a metered dose sprayer is attached. In one embodiment, the metered dose is delivered by drawing the pharmaceutical composition of the present invention into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

In a further aspect, the L-ergothioneine liposomes can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferring, targeted to a receptor in the blood-brain barrier; and the like. In another embodiment, the molecule can be administered intracranally or, more preferably, intraventricularly. In yet another embodiment, L-ergothioneine can be administered in a liposome targeted to the blood-brain barrier. These methods of delivery are particularly important since many debilitating brain diseases, such as Parkinson's, Alzheimer's, amyotrophic lateral sclerosis and possibly schizophrenia, have been linked to elevated ROS in the brain through a deficit in the mitochondrial enzyme complex 1.

A subject in whom administration of L-ergothioneine is an effective therapeutic regiment for mitochondrial protection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals. such as but not limited to bovine, equine, caprine, ovine, and porcine subjects, wild animals (whether in the wild or in a zoological garden), research animals, such as mice, rats, rabbits, goals, sheep, pigs, dogs, cars, etc., avian species, such as chickens, turkeys, songbirds, etc., i.e., for veterinary medical use.

The protection of mitochondria a from oxidative damage may be used for the prevention and treatment of a number of disorders, including effects of radiation to the body, disease processes, exposure to pollutants including tobacco combustion products, and protection against the damaging effects of certain pharmaceuticals whose mechanisms of action involve generation of ROS and other radicals. For example, certain anti-neoplastic agents induce oxidative radicals as their mechanism of action, but a significant and limiting side effect in patients is cardiotoxicity; higher doses and thus increased anti-cancer efficacy is achievable by protecting the mitochondria of the heart and other tissues with the compositions and methods of the present invention. In addition, various types of radiation used for anti-cancer therapy, as an alternative or adjunct to surgery, induces significant damage to tissues; prior administration of L-ergothioneine may be used to reduce or prevent the toxicity of radiation therapy to the body.

Furthermore, numerous disease processes involve ROS. In the eye, cataract, macular degeneration and degenerative retinal damage are attributed to ROS and may be treated with topical, oral or parentally-administered L-ergothioneine. A liposome formulation is preferred. ROS-related diseases of the lungs such as emphysema and bronchopulmonary dysphasia and including pathology induced by inhalation of tobacco combustion products and asbestos may be treated by an aerosolized form of L-ergothioneine as described above. Various diseases of the nervous system such as Parkinson's disease, Alzheimer's disease, muscular dystrophy, and multiple sclerosis may be treatable by oral or parenteral formulations or direct delivery to the central nervous system via intrathecal, intraventricular and intracranial administration. Iron overload diseases such as hemochromatosis and thalassemia may also be treated by the compositions and methods of the present invention. Other diseases include pancreatitis; diabetes; renal diseases including autoimmune nephrotic syndrome and heavy metal-induced nephrotoxicity; and radiation injuries.

In addition, destruction of mitochondria in non-target cells may be an unwanted side effect of cosmetic and sterilization treatment using light with endogenous or exogenous photosensitizers to generate ROS that destroy target tissue. For example, lasers for hair removal rely on generation of ROS in melanin-containing hair follicles. This may be augmented by delivery of a photosensitizing dye to the hair follicle. An unwanted side effect is the destruction of mitochondria in skin exposed to the light. Similarly, light is used in conjunction with photosensitizing dyes to inactivate viruses that contaminate blood products. An unwanted side effect is the destruction of mitochondria in the targeted blood cells.

In addition to the aforementioned therapeutic and prophylactic uses of the compositions of the present invention, various diagnostic utilities are also contemplated. The potential of L-ergothioneine to protect a mammal from mitochondrial damage and the level of L-ergothioneine necessary to afford protection may be assessed in vitro, exposing aliquots of a cellular sample from said mammal to the damaging agent or condition, said aliquots containing various concentrations of L-ergothioneine. The damage to mitochondria of the various aliquots is determined, as well as the lowest concentration, if any, of L-ergothioneine providing sufficient protection from damage. To determine the degree of therapeutic benefit of L-ergothioneine to a mammal after exposure to a mitochondrial damaging agent, a similar diagnostic test as described above may be employed, with a variation in that the various concentrations of L-ergothioneine, are applied to the cellular sample aliquots after exposure to the mitochondrial damaging agent. In another embodiment the extent of exposure of a mammal to ROS may be assessed by determining the effect of L-ergothioneine on a sample of cells taken from the mammal. These diagnostic utilities further offer assistance in selecting an effective therapeutic dose of L-ergothioneine.

In a further embodiment, the ability of L-ergothioneine to protect a cellular sample from the damaging effects of a therapeutic regimen that causes oxidative damage, such as an anti-neoplastic agent or radiation therapy to be administered to a mammal with cancer, can be performed in vitro by combining the anti-neoplastic agent with various concentrations of L-ergothioneine, applying the combination to identical aliquots of a cellular sample from a mammal, and determining the extent of mitochondrial damage in said series of samples. These data may be used to determine an effective dose of L-ergothioneine to prevent mitochondrial damage in the non-diseased cells of said mammal. In a parallel manner using a sample of diseased or cancerous cells from said mammal, it may be determined whether L-ergothioneine will effect any diminution of the anti-cancer activity of said anti-cancer agent; based on these two tests, a level of L-ergothioneine for co-administration with the anti-cancer agent may be selected to provide optimal protection of the non-diseased cells of the mammal from the anti-cancer agent while providing maximum anti-cancer therapy. These are non-limiting examples of useful diagnostic tests assessing the prophylactic and therapeutic benefits of the compositions and methods of the present invention.

They may be used, for example to determine the optimal concentration of L-ergothioneine to be used in conjunction with PDT or laser treatments.

Application of L-ergothioneine and its effect on mitochondrial damage is demonstrated by the following experimental example in which mouse keratinocytes are treated with unencapsulated or liposome-encapsulated L-ergothioneine. The mitochondria are then subjected to the potentially damaging effects of UV-B light and to alloxan (which is known to induce oxygen radicals) and the results measured. Damage to mitochondria was detected by two methods: 1) the MTT assay and 2) the JC-1 assay.

EXAMPLE I
UV-B Light

Mouse keratinocytes were pretreated with different concentrations of L-ergothioneine (unencapsulated) and then exposed to ultraviolet B radiation (UV-B), the shorter wavelength range of UV light present in sunlight which is responsible for significant photodamage to the skin. The light was generated by a FS20 sunlamp filtered with 2 sheets of Kodacel to eliminate light having a wavelength less than 280 nm.

MTT Assay

This assay measures the specific activity of mitochondria to cleave the tetrazolium ring of the soluble dye MTT [3-(4,5-dimethylthiazol-2-yl)-2,5-diphenyl tetrazolium bromide] to form the insoluble blue formazan form. Living mitochondria metabolize MTT and make the blue formazan; dead mitochondria immediately stop forming blue formazan. In the MTT assay, mammalian cells are pretreated with L-ergothioneine and then treated with the mitochondrial damaging agent, in this example UV-B. MTT is then added and the formation of the blue dye is measured spectrophotometrically.

Results

Table I provides the percent optical density of the formazan blue present relative to unexposed (control) mitochondria in cells for various UV-B levels, expressed as joules per square meter, and L-ergothioneine concentrations.

TABLE I

| UV-B | L-ergothioneine concentration | | | |
|---|---|---|---|---|
| J/m² | 0 mM | 0.1 mM | 0.5 mM | 1 mM |
| 0 | 100.0 | 100.0 | 100-0 | 100.0 |
| 100 | 84.2 | 95.7 | 97.2 | 97.1 |
| 200 | 80.7 | 97.0 | 99.4 | 103.9 |
| 500 | 79.9 | 91.0 | 90.8 | 96.0 |

These data show that in the absence of L-ergothioneine increasing UV-B irradiation intensity results in a decreasing numbers of living mitochondria in the keratinocytes, as shown by the dose-responsive decreasing level of conversion of MTT to formazan. Ultraviolet-irradiated keratinocytes are protected by L-ergothioneine: at 100 and 200 J/m² all three levels of L-ergothioneine have maintained greater than 95% mitochondrial viability; at the highest UV-B dose, L-ergothioneine still protected the mitochondria.

EXAMPLE 2
Alloxan

Mouse keratinocytes were pretreated with various concentrations of L-ergothioneine (unencapsulated) and then exposed to alloxan at various concentrations.

MTT

The effect of alloxan on the pretreated mitochondria was determined by the MTT assay as in Example 1.

Results

Table 2 provides the percent optical densities of the formazan blue present relative to unexposed (control) mitochondria in cells for various alloxan concentrations, and L-ergothioneine concentrations.

TABLE 2

| Alloxan | L-ergothioneine concentration | | | |
|---|---|---|---|---|
| (mM) | 0 mM | 0.1 mM | 0.5 mM | 1 mM |
| 0 | 100.0 | 100.0 | 100.0 | 100.0 |
| 0.625 | 81.6 | 86.3 | 88.3 | 91.2 |
| 1.25 | 76.5 | 80.8 | 81.0 | 86.5 |
| 2.5 | 77.1 | 81.1 | 81.0 | 82.9 |
| 5 | 69.2 | 73.3 | 73.3 | 67-8 |
| 10 | 70.7 | 74.9 | 74.1 | 68.5 |
| 20 | 74.5 | 79.1 | 78.4 | 72.7 |
| 40 | 69.2 | 73-3 | 72.3 | 66.6 |

Alloxan induces oxidative damage to mitochondria; a dose-responsive reduction in mitochondrial viability can be seen up to a level of 5 mM, above which the damage has plateaued. In the dose-responsive portion of the curve, L-ergothioneine afforded protection from oxidative damage.

EXAMPLE 3

Mouse keratinocytes were pretreated with L-ergothioneine, both unencapsulated and encapsulated in liposomes (prepared as described below), at a final concentration of 12.5 $\mu$M. A control group was not treated with L-ergothioneine. The mouse keratinocytes were then exposed to UV-B as in Example I.

Liposome Encapsulation

The L-ergothioneine was encapsulated into liposomes composed of phosphatidyl choline, phosphatidyl ethanolamine, oleic acid and cholesteryl hemisuccinate in a ratio of 2:2:1:5. To calculate the concentration of entrapped L-ergothioneine, the liposomes are extracted with chloroform, and the $OD_{258}$ is measured in the aqueous layer. The concentration of L-ergothioneine is calculated using the $\epsilon_{258}$ of L-ergothioneine of 14,500. The final concentration of L-ergothioneine in the purified liposome was about 1.1 mM. This concentration was reduced by diluting the liposomes with cell culture media to a final concentration of 12.5 $\mu$M in the media. Unencapsulated L-ergothioneine was adjusted to the same concentration by dilution.

The effect of the UV-B on the pretreated and untreated mitochondria was determined by the MTT assay as in Example 1.

Results

Table 3 provides the percent optical density of the formazan blue present in each case relative to unexposed (control) mitochondria in cells for various UV-B levels.

TABLE 3

| | L-ergothioneine at 12.5 $\mu$M | | |
|---|---|---|---|
| UV-B (J/m²) | Encapsulated L-ergothioneine | Unencapsulated L-ergothioneine | Without L-ergothioneine |
| 0 | 100.0 | 100.0 | 100.0 |
| 100 | 106.8 | 89.9 | 75.4 |
| 500 | 110.3 | 89.9 | 76.8 |

In the absence of L-ergothioneine, keratinocytes showed significant mitochondrial damage at both UV B doses.

Unencapsulated L-ergothioneine afforded significant but not complete protection under these conditions, active at concentrations as low as 12.5 μM. Complete protection was afforded by the encapsulated formulation of L-ergothioneine, at a concentration at which the unencapsulated L-ergothioneine was less than completely effective. Thus, the liposome formulation of L-ergothioneine provides superior protection.

EXAMPLE 4

Alloxan

Mouse keratinocytes were pretreated with L-ergothioneine (unencapsulated) at 1 mM and then treated with 8 mM alloxan. One day after treatment with L-ergothioneine, the cells were treated for 10 minutes with JC-I and the cells examined by fluorescence microscopy.

JC-1 Assay

The JC-1 assay makes use of the fluorescent dye JC-1 (5,5', 6,6'-tetrachloro-1, 1', 3,3'-tetrathylbenzimidazolecarbocyanine iodide) (Molecular Probes Inc., Eugene, OR). This dye immediately and specifically intercalates into mitochondrial membranes. In living, charged membranes the JC-1 dye is maintained in the membrane as a monomer, and fluoresces green. When the mitochondrial membrane is damaged, aggregation of the JC-1 dye into J-1 aggregates occurs and the fluorescence changes to orange. Orange coloration is then characteristic of mitochondrial membrane damage.

Results

Untreated control cells were predominantly green. Cells treated with alloxan alone showed significant patches of orange. Cells treated with alloxan and L-ergothioneine showed much less orange than cells treated with alloxani alone. Cells treated with L-ergothioneine alone showed green fluorescence.

Thus, using a different means of determining mitochondrial viability, the protection afforded mitochondria by L-ergothioneine is confirmed.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

I claim:

1. A method to selectively inactivate prokaryotic organisms intermingled with eukaryotic cells by treating the mixture with an effective concentration of L-ergothioneine to protect the mitochondria of the eukaryotic organisms and then exposing the mixture to radiation, radicals, or reactive oxygen species sufficient to inactivate the prokaryotic organisms.

2. The method of claim 1 wherein the radiation, radicals or reactive oxygen species are generated by agents selected from the group of: photodynamic therapy, photothermolysis, and lasers.

3. The method of claim 1 wherein the prokaryotic organism is a virus.

4. The method of claim 1 wherein the prokaryotic organism is the human immunodeficiency virus.

5. The method of claim 1 wherein the eukaryotic cells are selected from the group of white blood cells and red blood cells.

* * * * *